United States Patent
Zagame

[19]

[11] Patent Number: 5,998,693
[45] Date of Patent: Dec. 7, 1999

[54] FLEXIBLE ADHESIVE ELEMENT FOR EXTERNAL MEDICAL USE IN THE TREATMENT OF HYPERTROPHIC OR CHELOID SCARS FOLLOWING BREAST SURGERY

[76] Inventor: André Zagame, 55 rue de l'Eglise, 61110 Remalard, France

[21] Appl. No.: 08/849,452
[22] PCT Filed: Sep. 11, 1996
[86] PCT No.: PCT/FR96/01395
    § 371 Date: Jun. 17, 1997
    § 102(e) Date: Jun. 17, 1997
[87] PCT Pub. No.: WO97/09951
    PCT Pub. Date: Mar. 20, 1997

[30] Foreign Application Priority Data

Sep. 12, 1995 [FR] France ................................. 95 10656

[51] Int. Cl.⁶ .............................. A61F 13/00; A41C 3/00
[52] U.S. Cl. ............................................ 602/52; 450/81
[58] Field of Search .................................. 602/41–59, 17; 2/67; 450/55, 56, 57, 81, 30, 31, 32, 37, 38, 39, 40, 53; D2/701, 706; D24/189; 128/893, 894, 858; 623/7

[56] References Cited

U.S. PATENT DOCUMENTS

| | | |
|---|---|---|
| 2,437,886 | 3/1948 | Millard et al. ........................... 428/80 |
| 2,728,079 | 12/1955 | Williams .................................. 450/81 |
| 2,869,553 | 1/1959 | D'or ....................................... 450/81 |
| 3,280,818 | 10/1966 | Pankey et al. ............................ 450/81 |
| 3,934,593 | 1/1976 | Mellinger ................................. 450/81 |
| 4,195,639 | 4/1980 | Lee .......................................... 450/57 |
| 4,748,976 | 6/1988 | Cali ........................................ 604/289 |
| 4,754,750 | 7/1988 | Imonti . |
| 4,870,977 | 10/1989 | Imonti . |
| 4,992,074 | 2/1991 | Diaz ........................................ 450/81 |
| 5,584,883 | 12/1996 | Wild ......................................... 623/7 |
| 5,669,395 | 9/1997 | Thompson ............................. 128/846 |

FOREIGN PATENT DOCUMENTS

| | | |
|---|---|---|
| 482682 | 6/1948 | France . |
| 2505620 | 11/1982 | France .................................... 450/81 |

*Primary Examiner*—Richard J. Apley
*Assistant Examiner*—Kim M. Lee
*Attorney, Agent, or Firm*—Sixbey, Friedman, Leedom & Ferguson, PC; Stuart J. Friedman

[57] ABSTRACT

The flexible adhesive element (100) has a profile that is generally anchor-shaped, with an essentially rectilinear central branch (101) and with two curved side branches (102, 103). The central branch (101) is designed to extend to the peri-areolar zone of the breast concerned so as to cover said zone, and the two side branches (102, 103) are designed to extend along the fold beneath the breast to cover said fold at least in part.

9 Claims, 3 Drawing Sheets

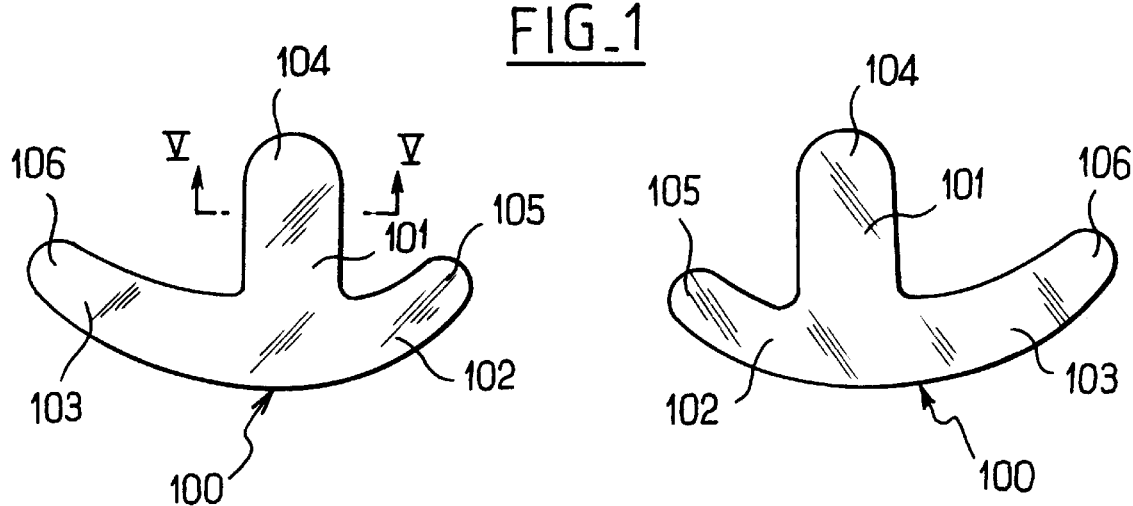
FIG_1
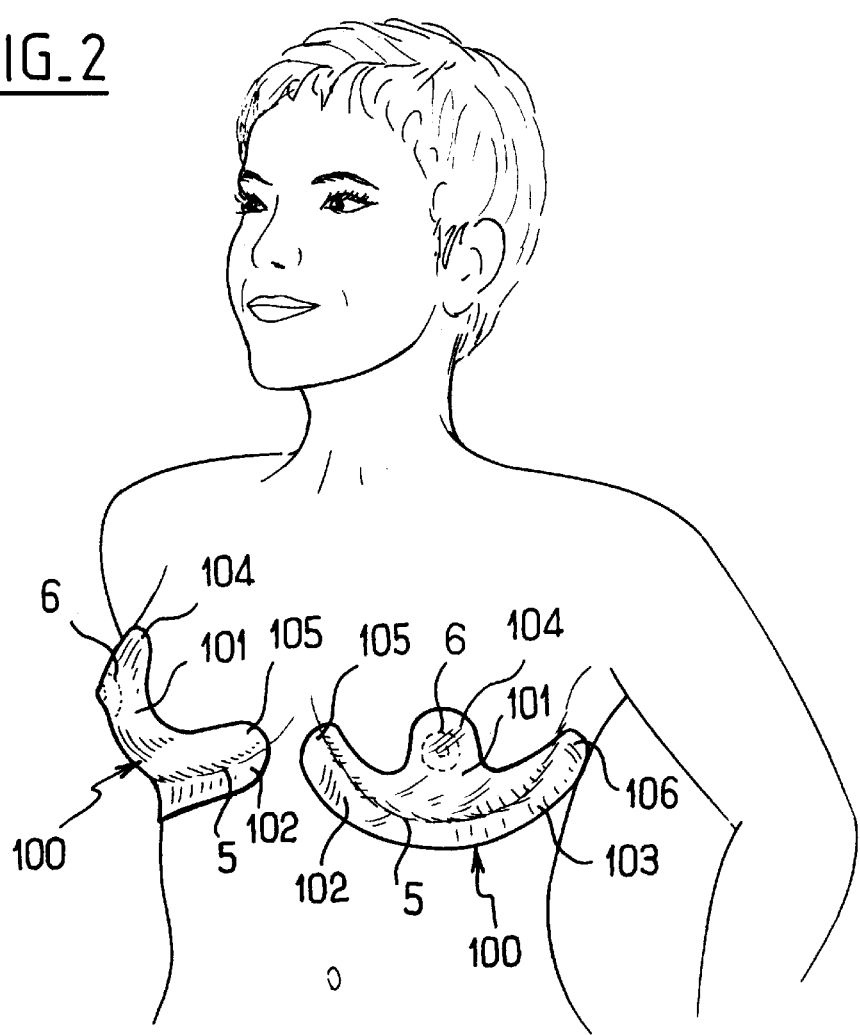
FIG_2

FIG_3
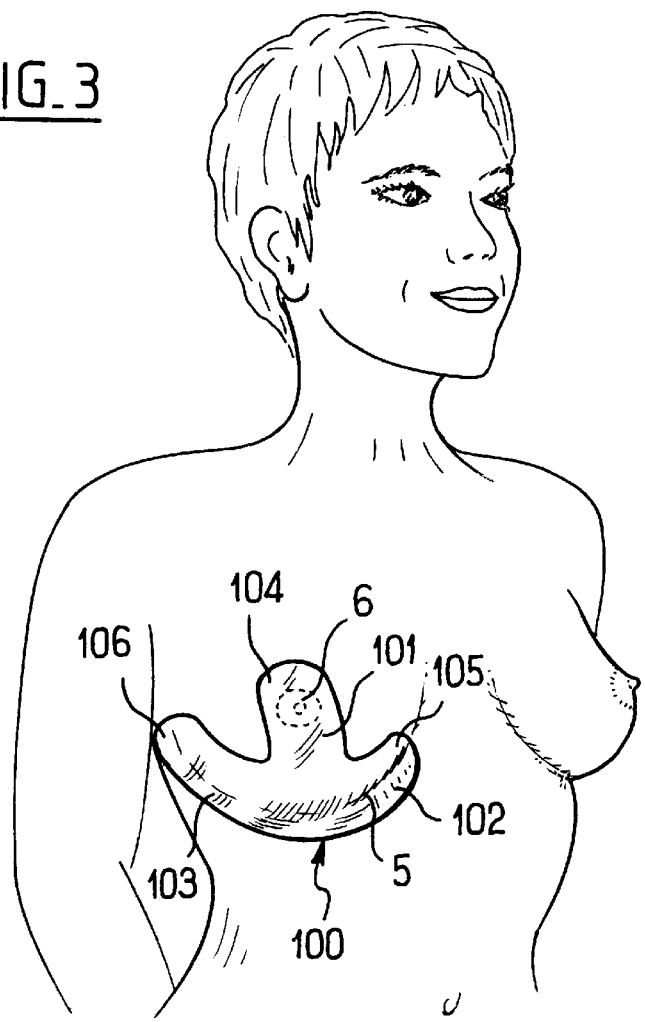
FIG_4
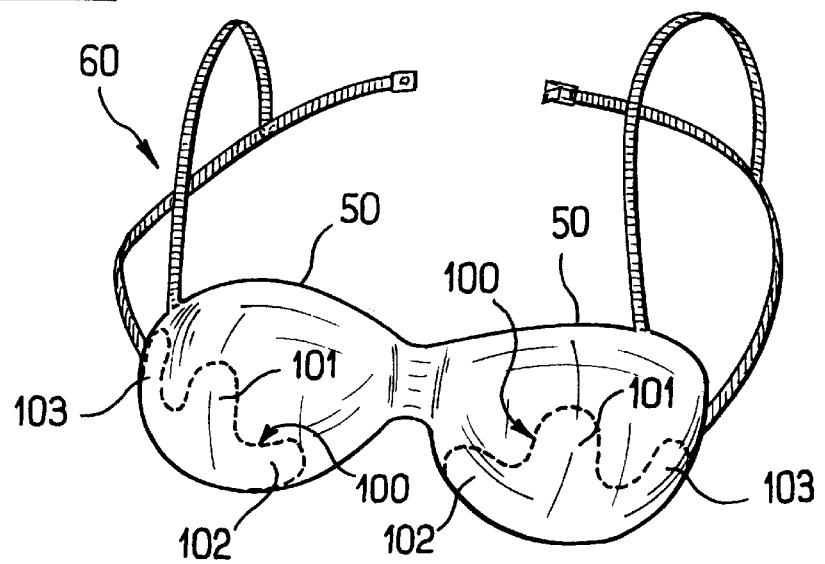

FLEXIBLE ADHESIVE ELEMENT FOR EXTERNAL MEDICAL USE IN THE TREATMENT OF HYPERTROPHIC OR CHELOID SCARS FOLLOWING BREAST SURGERY

The present invention relates to a flexible adhesive element for external medical use in the treatment of hypertrophic or cheloid scars following breast surgery.

BACKGROUND OF THE INVENTION

The state of the art is illustrated by document WO-A-88 06877 which describes an adhesive medical patch for protecting the nipple and the areolar zone of the breast following a surgical operation. The patch is circular and it is held in place by four adhesive tabs in a cross-configuration. As a result, the zone concerned of the breast is very limited.

To complete the state of the art, mention may also be made of other devices which are not for medical use, but which are designed to provide satisfactory support for the breast. These comprise, in particular, stick-on bra type devices (see for example documents FR-A-2 505 620 and U.S. Pat. No. 2,869,553) or devices of the molded shell type designed to serve as a stiffener that can be implanted in a traditional bra (see for example document BE-A-482 682).

Breast surgery, whether for repair purposes or for reconstruction purposes, requires the use of several types of surgical techniques, and the surgeon selects the technique which is most suited to the shape of the breast. Mention can be made of the peri-areolar technique which leaves a substantially circular scar in the areolar zone of the breast. There are also the L-technique and the T-technique which leave a scar formed by a first line going down from the peri-areolar zone of the breast to the fold under the breast, and a second line (straight or curved) extending along the fold under the breast, on one or both sides of the first line. The L- or T-technique can also be combined with the peri-areolar technique, in which case the first scar line is topped by a substantially circular scar.

Such scars are difficult to treat to obtain good appearance since the breast is a soft organ that is difficult to compress, particularly in its peri-areolar zone. Also, patients are naturally disinclined to use a rigid or semi-rigid element or a strap partially or completely surrounding the bust in order to exert localized pressure on the scar zones.

It can then be tempting to use a flexible element of the same type as is used already for the treatment of scars in a zone of the body having bony support, but that leads to several difficulties.

For example, flexible elements are known that are made from a non-adhesive gel based on silicone or on three-block copolymers, said gels for medical use generally being packaged in the form of patches, bands, or strips. Such patches, bands, or strips present advantageous flexibility, but they are thick (3 mm to 5 mm in general), which spoils appearance, and they require additional means to put them into position and to hold them in place (adhesive strips, etc.), such that applying such flexible elements to the treatment of breast scars would give rise to considerable risk of undesirable movement giving rise to poor positioning relative to the patient's bust, and consequently to reduced therapeutic effect. In addition, and particularly with bands, they also exert pressure on an area which is not limited to the scar zone that is to be treated, and that presents a major drawback of the element's occlusive effect and because of the resulting risk of maceration. Consequently, such a flexible element appears to be difficult to apply in treating scars following breast surgery.

Flexible elements are also known that are constituted by a silicone-based film having one face coated in an adhesive gel based on silicone (see for example document U.S. Pat. No. 4,991,574). These are dressings for applying to open wounds or to scars, which dressings are cut from a rectangular patch which is generally 10 cm×15 cm. However, that type of flexible element is also relatively thick (generally at least 3 mm to 4 mm), and of very limited flexibility; such that the traumatizing nature of wearing such an element is further reinforced because it is conspicuous. The poor flexibility of an element of that type makes it difficult to fit to the shape of a curved or complex surface, such that it would appear to be unsuitable for use in treating scars following breast surgery. Its great thickness is also an unfavorable factor from the points of view of appearance and of comfort, which is particularly important for the bust area. Finally, that product is relatively fragile and its lifetime is no more than about 2 weeks, which makes it expensive.

OBJECTS AND SUMMARY OF THE INVENTION

An object of the invention is to provide a flexible adhesive element for providing effective treatment of hypertrophic or cheloid scars following breast surgery, and avoiding the drawbacks of the above-mentioned flexible elements.

Another object of the invention is to provide a flexible element of the adhesive type which is effective with different types of breast scar, depending on the type of surgery performed on the patient.

More particularly, the invention provides a flexible adhesive element for external medical use in the treatment of hypertrophic or cheloid scars following breast surgery, the element being characterized in that its profile is generally anchor-shaped, with an essentially rectilinear central branch and two curved side branches, the central branch being designed to extend to the peri-areolar zone of the breast concerned so as to cover said zone, and the two side branches being designed to extend along the fold beneath the breast concerned so as to cover said fold at least in part, with a first branch being for the portion of the fold that goes towards the sternum zone of the patient, and a second branch being for the portion of the fold that goes towards the axillary zone of the patient.

Such a flexible element is thus very versatile with respect to the surgical techniques used, whether they be peri-areolar techniques and/or L- or T-techniques. It thus becomes possible to recommend the use of such a flexible adhesive element under all circumstances after breast surgery, without requiring cutting out specific to circumstances.

Preferably, the central branch is terminated in a rounded end portion covering all of the areolar zone of the breast concerned, and is of a width that is essentially constant and the same as that of its rounded end portion. This ensures that the same element is equally suitable for covering a scar whether following surgery by a peri-areolar technique and scar lines or following surgery by an L- or a T-technique going down from the peri-areolar zone of the breast to the fold beneath the breast.

Advantageously, the first side branch is shorter than the second side branch, the second side branch extending to the axillary zone of the patient. In particular, the side branches are of essentially constant width and terminate in respective rounded end portions. The special shape of the side branches of the flexible element thus ensures optimum covering of the zone concerned of the fold beneath the breast for all kinds of scar following surgery implemented using an L-technique or a T-technique.

Preferably, the flexible element is constituted by a support layer on which there is fixed a layer of gel that is adhesive throughout. In a variant, a support layer has fixed thereon a layer of gel that is essentially non-adhesive, with the free face thereof being covered in a film that is adhesive on its outside face.

The material constituting the support layer is selected from the group constituted by textile materials, optionally elastic textile materials, plastics materials, treated papers, and essentially non-adhesive flexible gels.

In a first application of the invention, the above flexible element has an adhesive face designed to be applied against the body of the patient, said adhesive face being optionally covered in a protective film which is removed immediately before the flexible element is put into place.

In a variant application, the flexible element has an adhesive face which is designed to be applied to the inside face of a bra cup for which the flexible adhesive element then constitutes a lining.

BRIEF DESCRIPTION OF THE DRAWINGS

Other characteristics and advantages of the invention appear more clearly in the light of the following description and the accompanying drawings, relating to particular embodiments, and in which:

FIG. 1 shows two flexible adhesive elements of the invention laid flat, and suitable for being applied respectively to a right breast and to a left breast;

FIG. 2 shows a patient wearing an anchor-shaped flexible element of FIG. 1 on each breast;

FIG. 3 is another perspective view of a patient wearing such a flexible adhesive element on her right breast only;

FIG. 4 is a perspective view of a conventional type of bra in which both cups are internally lined with a flexible adhesive element, each flexible element thus constituting a lining for the cup concerned.

MORE DETAILED DESCRIPTION

Figure 5A:
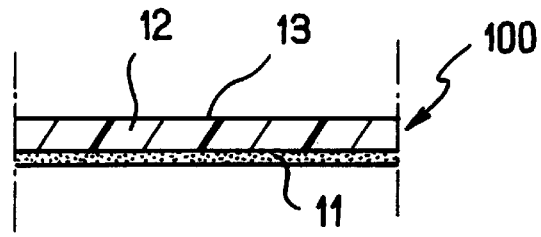
FIGS. 5A, 5B, 5C, 5D, 5E, and 5F are sections on V—V through a flexible adhesive element as shown in FIG. 1, and showing various embodiments of said flexible element, with support layers of different materials and with gel layers that are adhesive throughout or that are essentially non-adhesive.

FIG. 1 shows two flexible adhesive elements 100 of the invention, the left element being suitable for placing on a right breast and the right element on a left breast. Each flexible element 100 is generally anchor-shaped, having an essentially rectilinear central branch 101 and a first curved side branch 102 and a second curved side branch 103. In this case, the central branch 101 terminates in a rounded end portion 104, and it is of essentially constant width, which is the same as the width of the rounded end portion 104.

As can be seen more clearly in FIGS. 2 and 3, the central branch 101 of the flexible element 100 is designed to extend to the peri-areolar zone of the breast concerned so as to cover said zone, the rounded end portion 104 covering the entire areolar zone 6 of the breast. The two curved side branches 102 and 103 are designed to extend along the fold 5 beneath the breast concerned, so as to cover said fold, at least in part. Each flexible element 100 thus includes a the first curved side branch 102 for the portion of the fold beneath the breast going towards the sternum zone of the patient, and the second curved side branch 103 for the portion of said fold that goes towards the axillary zone of the patient. Specifically, it can be seen that the first curved side branch 102 is shorter than the second curved side branch 103, which extends all the way to the axillary zone of the patient. This asymmetry of the flexible elements does perhaps constitute a slight drawback insofar as it is necessary to make and store left elements and right elements, however this slight drawback is largely compensated by the advantage of each flexible element being easy to fit very accurately to the morphology of the patient. In addition, the longer side branch extending to the axillary zone of the patient makes it possible to hold the flexible element well relative to a vertical line going down from the areola of the breast, such that said zone, and the zone connecting it to the fold under the breast always remains properly covered by the flexible elements, in spite of the patient moving. It will also be observed that the curved side branches 102 and 103 are of essentially constant width in this case, and terminate in respective rounded end portions 105 and 106. In practice, a width is selected that is sufficient to be certain of properly covering all of the portion concerned of the fold 5 under the breast.

FIGS. 2 and 3 show a first way in which the flexible element 100 of the invention can be used, in which the adhesive face of the flexible element is applied directly to the body of the patient. In this case, each flexible element holds itself in place, without there being any need to provide external holding means. In addition, insofar as the structure of the flexible element is selected to be thin, this flexible element is extremely inconspicuous and enables the person to wear her usual bra.

In another way of using the invention, the adhesive face of the flexible element 100 is designed to be pressed against the inside face of a bra cup so that the flexible adhesive element constitutes a lining for the bra. Such a variant is shown in FIG. 4 in which there can be seen a conventional type of bra 60 with at least one of its two cups 50 (in this case both cups) being internally lined with a flexible adhesive element 100 like those described above. In this case, the, or each, cup which is lined with a properly positioned flexible element enables the flexible element(s) used to be positioned naturally and automatically as soon as the bra is put on. Application in this way is advantageous insofar as it enables the patient to use her usual bra in a manner that is so unobtrusive that, once the bra has been put on, she can forget she is wearing a therapeutic element.

Various structures are described below with reference to FIGS. 5A to 5F showing embodiments of flexible adhesive elements 100 made up of superposed layers.

Figure 5B:
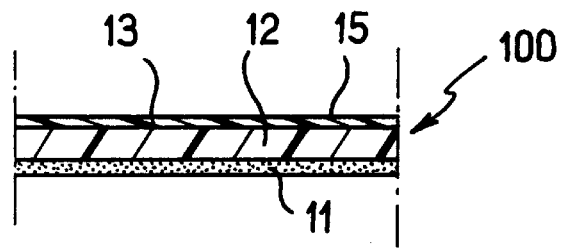

In FIG. 5A, the flexible adhesive element 100 is constituted by a support layer 11 made of textile material, on which there is fixed a layer 12 of gel for external medical use, which gel is adhesive throughout. In this case, the free face, referenced 13, of the layer 12 of adhesive gel is itself adhesive. As shown in FIG. 5B, it is more convenient in practice to provide for the free face 13 of the layer 12 of adhesive gel to be covered in a protective film 15, e.g. of plastics material, which film is removed immediately before the flexible adhesive element 100 is put into place. It may be constituted by a simple peel-off film analogous to those found on numerous adhesive products in the medical field. The presence of such a protective film 15 is particularly advantageous when the free face of the layer of adhesive gel is to be applied directly to the body of the patient. The textile material constituting the support layer 11 may be made of cloth, and optionally an elastic cloth, thereby obtaining a flexible element which is also compressive.

Although several adhesive gels can be envisaged for making the layer 12 of gel that is adhesive throughout, there follows a description of a particular composition of adhesive gel which has been found to be particularly satisfactory for making the flexible adhesive element of the invention.

In this particular composition, the adhesive gel of the layer 12 is made from at least one block copolymer based on styrene and on isoprene in a solvent-forming pharmaceutical inorganic oil, and of a hydrocarbon resin used in predetermined proportion in said gel, which proportion is selected to confer the desired degree of adhesion to the gel. The particular above-mentioned copolymer(s) selected make it possible to obtain a gel that is soft to a greater or lesser extent, lending itself particularly well to being shaped three-dimensionally. Also, the amount of hydrocarbon resin selected for use in the adhesive gel makes it possible to achieve the desired degree of adhesion that is best suited to the particular application concerned. Preferably, a gel is used that is made from at least one linear block copolymer based on styrene and on isoprene including about 15% by weight of styrene, said polymer or said mixture of copolymers essentially constituting 5% to 40% by weight of the adhesive gel. By way of example, mention can be made specifically of the linear block copolymer based on styrene and on isoprene and sold under the name KRATON D-KX 601 CS by Shell Chemical Company (KRATON® is a registered trademark of Shell). It is then preferable to use a light paraffin oil such as the oil sold under the trademark ONDINA 15® by the Shell Oil Company. The resin may be the resin under the name REGALITE R 101 by Hercules S.A. (REGALITE® is a registered trademark).

Figure 5C:
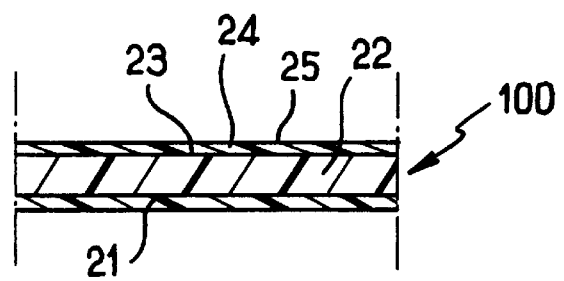

FIG. 5C shows another flexible adhesive element 100 of the invention in which the support layer 21 is a film of plastics material, or a sheet of treated paper (e.g. grease-proof paper). In this case, the layer of gel 22 is essentially non-adhesive, so it is necessary to provide for a film 24 that is adhesive on its own outside face 25 to be applied to the free face 23 of the layer 22. The non-adhesive gel may be a gel based on silicone or based on tri-block copolymers. By way of example, mention can be made of gels based on styrene-ethylene/butylene-styrene block copolymers in an inorganic oil. Mention may also be made of gels based on styrene-ethylene/butylene-styrene block copolymers made using KRATON® G 1650, 1651, 1652, and 1654 (where KRATON® is a registered trademark of Shell).

Figure 5D:
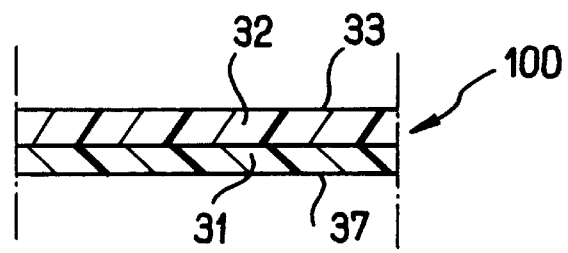

FIG. 5D shows another variant in which the support layer 31 is made of an essentially non-adhesive flexible gel, e.g. a gel of the above-mentioned type based on styrene-ethylene/butylene-styrene block copolymers in a light inorganic oil. A layer 32 of gel that is adhesive throughout is then fixed to said support layer 31. This adhesive layer may comprise the particular composition mentioned above with reference to FIG. 5A as the gel which is adhesive throughout. In this case, the free face 37 of the flexible element 100 is non-adhesive while the other free face 33 is adhesive. For the non-adhesive gel, it is possible, for example, to use a gel such as that sold under the name KRATON G 1654 X by Shell Chimie (KRATON® is a trademark registered by Shell). In a variant, it will be possible to use another KRATON G sold by the same company, such as KRATON G 1651 which differs from the above in terms of styrene content.

Figure 5E:
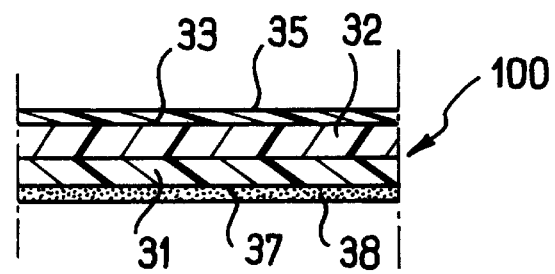

FIG. 5E shows a variant of FIG. 5D in which the free face 33 of the layer 32 of gel that is adhesive throughout is coated in a protective film 35 which is removed immediately before the flexible adhesive element is put into place, and the outside face 37 of the support layer 31 is covered in a protective layer 38 of cloth to avoid grease marks on a garment coming into contact with the outside surface of the flexible element.

Figure 5F:
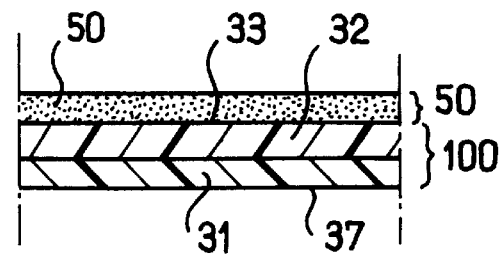

FIG. 5F shows another variant of FIG. 5D in which the outside face 37 of the support layer 31 of essentially non-adhesive flexible gel is designed to be applied to the zone concerned of the patient's body, while the free face 33 of the layer 32 of adhesive gel is applied against the inside face of the cup 50 of a bra, so that the flexible adhesive element then constitutes a lining therefore, as described above with reference to FIG. 4.

A flexible adhesive element is thus provided which is particularly effective in the treatment of breast scars, whatever the type of technique used during the surgery. In all cases, the element is pressed closely against the skin of the patient, thereby achieving an optimum therapeutic effect for the treatment of scars. In addition, the flexible adhesive element is discrete and comfortable to wear because it is thin and very flexible, providing advantageous components are selected such as those given above by way of example.

The invention is not limited to the embodiments described above, but on the contrary covers any variant reproducing the essential characteristics mentioned above by using equivalent means.

I claim:

1. A flexible adhesive element for external medical use in the treatment of hypertrophic or cheloid scars following breast surgery, comprising an adhesive element having a generally anchor-shaped profile, with an essentially rectilinear central branch together with first and second curved side branches, said central branch being adapted to extend to a peri-areolar zone of a breast so as to cover said peri-areolar zone during use, and said first and second curved side branches being adapted to extend along a fold beneath said breast when in use so as to cover said fold at least in part, with said first branch being adapted to extend along one portion of the fold in a direction of a sternum zone of the patient, and said second branch being adapted to extend along another portion of the fold in a direction of and up to an axillary zone of the patient, said first curved side branch being shorter than said second curved side branch, and each of said first and second curved side branches being of essentially constant width and terminating in respective round end portions.

2. The flexible element according to claim 1, wherein the central branch is terminated in a rounded end portion adapted to cover all of an areolar zone of said breast during use.

3. The flexible element according to claim 2, wherein the central branch has a width that is essentially constant and the rounded end portion thereof has a maximum width that is equal to the width of said central branch.

4. The flexible element according to claim 1 wherein it is constituted by a support layer on which there is fixed a layer of gel that is adhesive throughout.

5. The flexible element according to claim 1, wherein it is constituted by a support layer on which there is fixed a layer of gel that is essentially non-adhesive, with the free face thereof being covered by a film that is adhesive on its outside face.

6. The flexible element according to claim 4 or 5, wherein the material constituting the support layer is selected from the group consisting of textile materials, elastic textile materials, plastics materials, treated papers and essentially non-adhesive flexible gels.

7. The flexible element according to claim 4 or 5, wherein it has an adhesive face adapted to be applied against the body of the patient in use.

8. The flexible element according to claim 7 wherein said adhesive face is covered by a protective film which is adapted to be removed immediately before said flexible element is applied against the body of the patient.

9. The flexible element according to claim 4 or 5, wherein it has an adhesive face which is adapted to be applied to the inside face of a bra cup for which the flexible adhesive element then constitutes a lining.

* * * * *